(12) United States Patent
Hossein-Zadeh (10) Patent No.: US 11,933,732 B2
(45) Date of Patent: Mar. 19, 2024

(54) INTERFEROMETRIC SENSOR BASED ON SLAB WAVEGUIDE

(71) Applicant: UNM Rainforest Innovations, Albuquerque, NM (US)

(72) Inventor: Mani Hossein-Zadeh, Albuquerque, NM (US)

(73) Assignee: UNM Rainforest Innovations, Albuquerque, NM (US)

(*) Notice: Subject to any disclaimer, the term of this patent is extended or adjusted under 35 U.S.C. 154(b) by 193 days.

(21) Appl. No.: 17/471,139

(22) Filed: Sep. 9, 2021

(65) Prior Publication Data

US 2021/0404969 A1 Dec. 30, 2021

Related U.S. Application Data

(63) Continuation of application No. 15/743,204, filed as application No. PCT/US2016/041784 on Jul. 11, 2016, now abandoned.

(Continued)

(51) Int. Cl.
| | |
|---|---|
| *G01N 1/00* | (2006.01) |
| *G01J 3/02* | (2006.01) |
| *G01J 3/42* | (2006.01) |
| *G01J 3/453* | (2006.01) |
| *G01N 21/77* | (2006.01) |
| *G01N 33/543* | (2006.01) |
| *G02B 6/122* | (2006.01) |
| *G02B 6/125* | (2006.01) |

(52) U.S. Cl.
CPC ........ *G01N 21/7703* (2013.01); *G01J 3/0224* (2013.01); *G01J 3/0256* (2013.01); *G01J 3/42* (2013.01); *G01J 3/453* (2013.01); *G01N 33/54373* (2013.01); *G02B 6/1223* (2013.01); *G02B 6/1225* (2013.01); *G02B 6/125* (2013.01); *G01N 2201/0638* (2013.01)

(58) Field of Classification Search
None
See application file for complete search history.

(56) References Cited

U.S. PATENT DOCUMENTS 7,181,120 B2 2/2007 Sugitatsu et al.
10,610,846 B2 * 4/2020 Chakravarty ........ B01J 19/0046

OTHER PUBLICATIONS

Cross et al; The metrics of surface adsorbed small molecules on the Young's fringe dual-slab waveguide interferometer; Journal of Physicas D: Applied Physics, vol. 37 74; IOPscience; UK.

(Continued)

*Primary Examiner* — Jyoti Nagpaul
(74) *Attorney, Agent, or Firm* — Keith Vogt, Ltd.; Keith A. Vogt (57) ABSTRACT

The present invention provides a sensor having, one or more optical slab waveguides having one or more target regions. The target regions may interact with gas molecules or trap, entrain or capture one or more targets of interest. The optical slab waveguides are adapted to receive one or more input optical beams from one or more light sources to create a plurality of propagating optical waves in optical slab waveguide. The propagating optical waves interact with said one or more target regions to create an optical output wavefront that may be in the form of a diffraction pattern. The target regions may be functionalized with an antibody, polymer, cell, tissue, or biological material.

20 Claims, 5 Drawing Sheets

Related U.S. Application Data (60) Provisional application No. 62/190,346, filed on Jul. 9, 2015.

(56) References Cited

OTHER PUBLICATIONS

Federal Institute of Industrial Property; International Written Opinion and Search Report for PCT/US2016/041784; dated Nov. 3, 2016; 9 pages; Moscow, RU.

* cited by examiner

Single-source single-waveguide input

FIG. 4A

Single-source multi-waveguide input

FIG. 4B

Multi-source multi-waveguide input

INTERFEROMETRIC SENSOR BASED ON SLAB WAVEGUIDE

RELATED APPLICATIONS

This application is a continuation of U.S. Ser. No. 15/743,204 filed Jan. 9, 2018, which is a 371 National Phase of PCT/US2016/041784 filed Jul. 11, 2016, which claims the benefit of U.S. Provisional Application No. 62/190,346 filed Jul. 9, 2015 all of which are herein incorporated by reference.

BACKGROUND OF THE INVENTION

Label free photonic detection of biomarkers is typically achieved using optical transduction techniques that translate small variations of optical phase variations, due to molecular binding events, to measurable signals. Both resonant and non-resonant optical configurations are capable of converting minute optical phase variations to measurable optical power (amplitude) changes. In non-resonant sensors, light travels in two different optical paths where the refractive index of one path changes as molecules are trapped on the path using an immune affinity technique. As such, the interference between these the beams passing through these two paths (one passive and one active) results in an optical out power change that is proportional to the index change (and therefore biomarker concentration) in the active path. These optical paths are typically single mode waveguides (1-2 microns in width and less than 1 micron thick).

The resonant approach is also based on interference but using one beam that passes multiple times through a closed optical path inside a microresonator (usually a circular inside a microring resonator) and interferes with itself. In this case, the entire optical path is sensitive and as biomarkers are trapped on the resonator surface, the resonant wavelength shifts. The resonant approach has orders of magnitude larger sensitivity compared to the non-resonant approach but it suffers from the following problems: 1) usually a tunable and narrow linewidth optical source is required to interrogate the sensor; 2) fabrication of high quality (required for high sensitivity) optical microresonators is difficult and expensive; 3) the active area on the resonator is very small and therefore at low concentrations the time required for detection is long (due to low probability of binding events on the small number of binding sites available on the microresonator surface); 4) each device can only be functionalized with one type of antibody and therefore only detect one type of molecule (both due to its small size and the detection mechanism); 5) the quality factor (and therefore the sensitivity) of the resonator easily degrades over time and by a very small amount of surface contaminations.

BRIEF SUMMARY OF THE INVENTION

The present invention does not suffer from the above mentioned problems associate with resonant optical sensing but can still offer the same level of sensitivity. In one embodiment, instead of having one beam making several round trips over the same optical path, the input optical beam from an optical power source is effectively split into a plurality of optical beams by a slab. The optical path for each one of the beams may have a different degree of sensitivity to a target of interest which may be biomarker concentration and accomplished by functionalizing different lengths of each path using antibodies or other agents.

In another embodiment, the present invention provides a sensor that does not require a tunable and narrow linewidth optical source.

In another embodiment, the present invention provides a high sensitivity optical sensor that is easy to fabricate.

In another embodiment, the present invention provides a sensor that does not have long detection times for low concentration target molecules.

In another embodiment, the present invention provides a sensor that may be made from a large variety of materials.

In another embodiment, the present invention provides a sensor having, one or more optical slab waveguides having one or more target regions. The target regions may interact with gas molecules. In other embodiments the target regions may be adapted to trap, entrain or capture one or more targets of interest. The optical slab waveguides are adapted to receive one or more input optical beams from one or more light sources to create a plurality of propagating optical waves in optical slab waveguide. The propagating optical waves interact with said one or more target regions to create an optical output wavefront that may be in the form of a diffraction pattern. The target regions may be functionalized with an antibody, polymer, cell, tissue, or biological material.

In yet other embodiments of the present invention, a plurality of spaced apart target regions provided which are separated by non-functionalized regions. In addition, the propagating optical waves may have different degrees of sensitivity to a target of interest as a result of the spaced apart target regions being separated by non-functionalized regions. The target region may also have different configurations or be in the form of different patterns.

In yet other embodiments of the present invention, one or more optical manipulators may be used to transform the optical wavefront prior to conversion into an electronic signal by one or more photodetector arrays. The photodetector arrays may be charge coupled devices and the optical manipulators include filters, lens, polarizers and/or masks or combinations thereof. The optical manipulators may be used to separate the optical wavefront into different angular frequencies or modulate the phase and amplitude of the optical wavefront.

In yet other embodiments of the present invention, one or more arrangements that increase the length of propagating optical waves may be provided. The arrangements may be configured to recirculate the propagating optical waves in the slab waveguide. In other embodiments, the arrangements may be air-filled openings the waveguide that partially reflect the propagating optical waves.

In yet other embodiments, the present invention provides one or more optical slab waveguides having one or more target regions where the target regions interact with one or more targets of interest, which may be one or more gas molecules. The optical slab waveguides are adapted to receive one or more input optical beams from one or more light sources to create a plurality of propagating optical waves in the optical slab waveguides. The propagating optical waves interact with said one or more target regions to create an optical output wavefront. In other embodiments, the target regions include one or more functional polymers that interact with target gas molecules to change the optical absorption or refractive index of the functional polymers. In other aspects, the target regions include one or more functional polymers that directly interact with target gas molecules, whereby the interaction between the gas and polymers modifies the optical optical absorption or refractive index of the polymers.

In yet other embodiments, the present invention provides one or more optical slab waveguides which may be adapted to receive one or more input optical beams from one or more light sources to form one or more propagating optical waves. The optical slab waveguides interact with acoustic waves to create one or more strain patterns over the slab which varies the refractive index of the slab to create detectable variations in the output wavefront which may form a diffraction pattern. In addition, one or more arrangements that increase the length of said propagating optical waves may be used. The arrangements recirculate the propagating optical waves in the slab waveguide or are air-filled openings in the waveguide that partially reflect the propagating optical waves. The arrangements may also be used to tailor the acoustic frequency response of the sensor.

Additional objects and advantages of the invention will be set forth in part in the description, which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

In the drawings, which are not necessarily drawn to scale, like numerals may describe substantially similar components throughout the several views. Like numerals having different letter suffixes may represent different instances of substantially similar components. The drawings illustrate generally, by way of example, but not by way of limitation, a detailed description of certain embodiments discussed in the present document.

DETAILED DESCRIPTION OF THE INVENTION

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a representative basis for teaching one skilled in the art to variously employ the present invention in virtually any appropriately detailed method, structure or system. Further, the terms and phrases used herein are not intended to be limiting, but rather to provide an understandable description of the invention.

In one embodiment, the present invention provides a sensor having a slab waveguide layer and a trapping layer which may be an antibody (or other substance that has an affinity to a target substance), one or more biological materials such as cells or tissue as well as one or more functional polymers. Trapping layer may be located on high index waveguide layer or slab above which an evanescent optical field is formed that interacts with the trapping layer and the trapped molecules or the functional polymers. Substrate may also be provided.

Figure 1A:
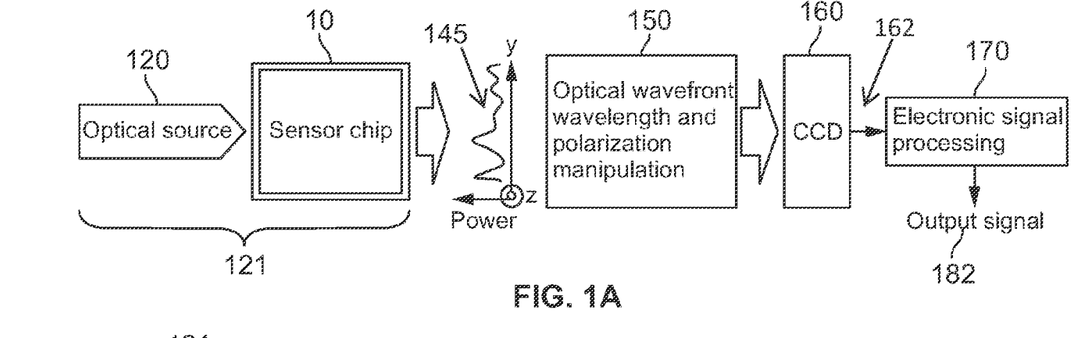
FIG. 1A is a schematic diagram showing different stages of the sensor system for an embodiment of the present invention.
Figure 1B:
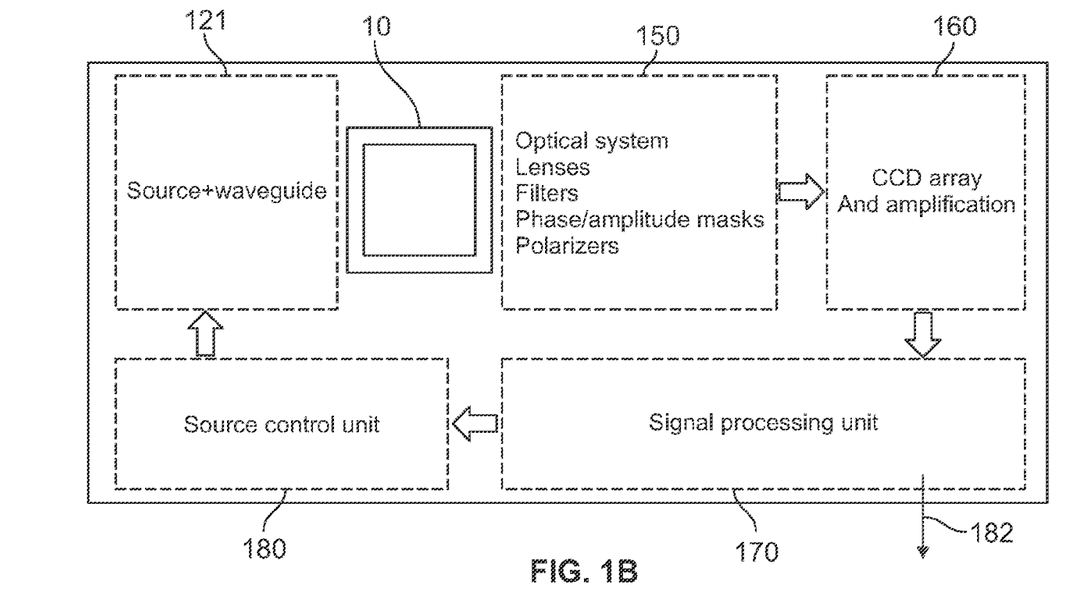
FIG. 1B depicts a system level design for an embodiment of the present invention.
Figure 2:
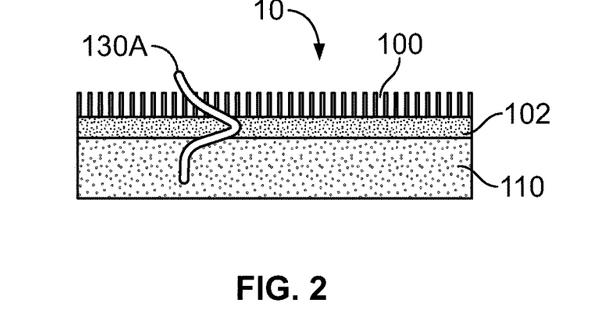
FIG. 2 is a schematic diagram showing a side view of a sensor for an embodiment of the present invention.
Figure 3:
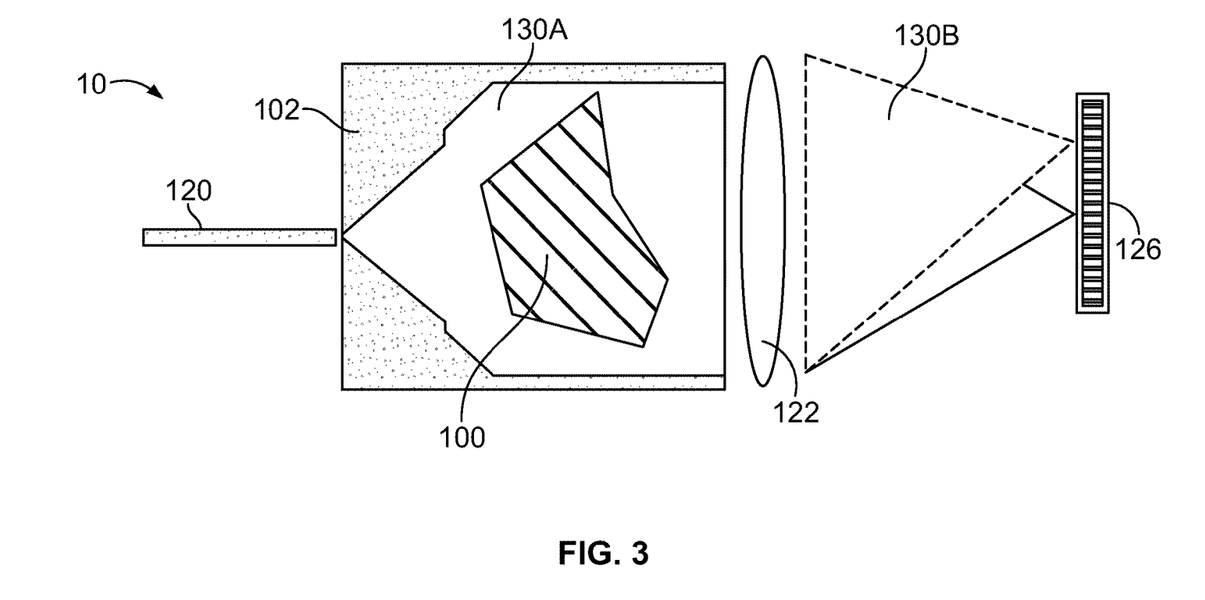
FIG. 3 is a schematic diagram showing a top view of a sensor for an embodiment of the present invention.

As shown in FIGS. 1A and 1B, as well as FIGS. 2-3, in one preferred embodiment, the present invention provides a sensor 10 having a trapping layer 100 which may be an antibody or other substance that has an affinity to a target substance. Trapping layer 100 may be located on high index waveguide layer or slab 102 in which an evanescent field 130A is formed that interacts with the trapping layer. Substrate 110 may also be provided.

Slab waveguide 102 may be combined with an optical power source 120, which may be integrated or fiber based, for launching optical power to create a plurality of optical modes in the slab waveguide. Antibody/trapping layer 100 may be distributed over the slab with a predetermined pattern that optimizes the impact of surface index change on the device output 130B through lens 122 (or possibly a plurality of lenses) to photodetector (CCD) array 126.

As also shown in FIGS. 1A and 1B, waveguide 10 and optical source 120 may be combined as a unit 121 that creates an optical wavefront 145 that may be manipulated by one or more optical manipulators such as filters, lens, polarizers and/or masks or combinations thereof 150. The two-dimensional optical wavefront is then converted into an electronic signal by one or more CCD arrays and amplifiers 160 which output an electronic signal for further processing by signal processing unit 170 which is also in communication with source control unit 180. An output signal 182 is also generated as shown.

Figure 4A:
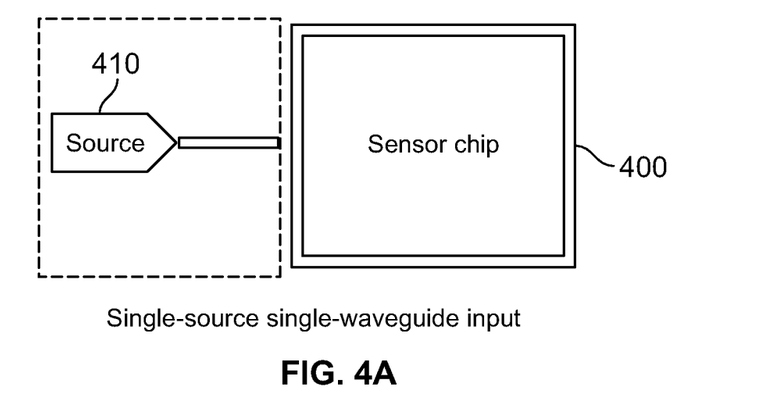
FIGS. 4A, 4B and 4C show several configurations for launching optical power to a slab waveguide for various embodiments of the present invention.
Figure 4B:
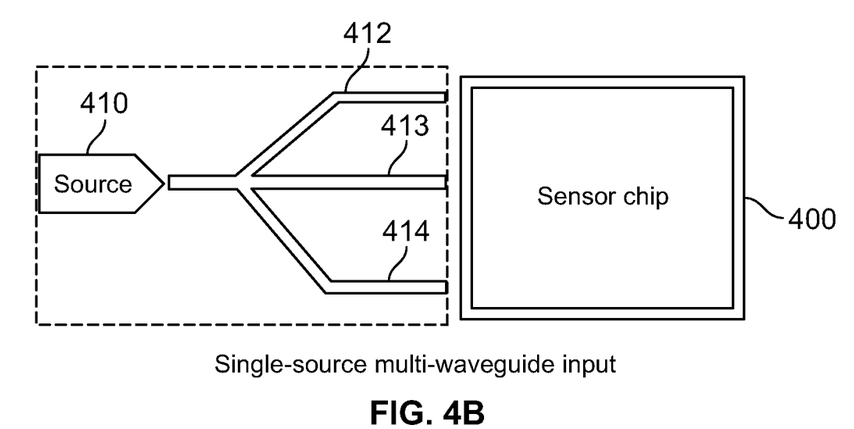
Figure 4C:
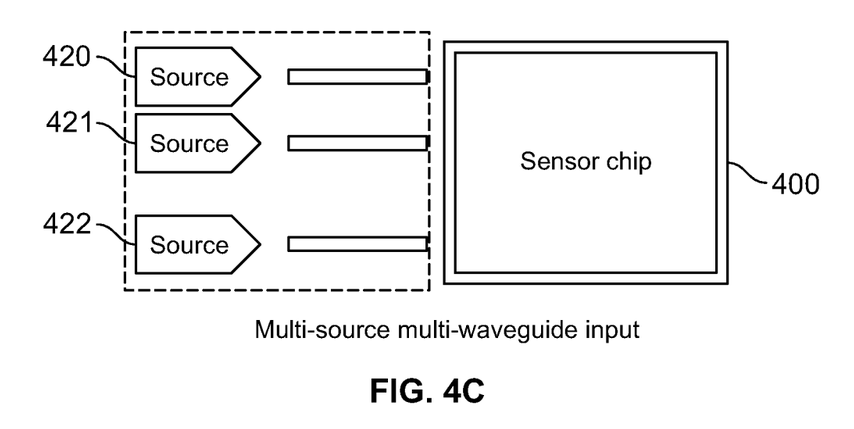

As shown in FIGS. 4A-4C, the optical modes in the waveguide layer 400 may be excited in a variety of ways. As shown in FIG. 4A, a single optical power source 410 may be used. As shown in FIG. 4B, in another embodiment of the present invention, the input optical beam from one or more optical power sources 410 is effectively split into a plurality of optical beams 412-414 by using a fiber-based or integrated optical power splitter. In yet other embodiments, as shown in FIG. 4C, multiple power sources 420-422 may be used with one or more of the beams being further split as described above.

Figure 5A:
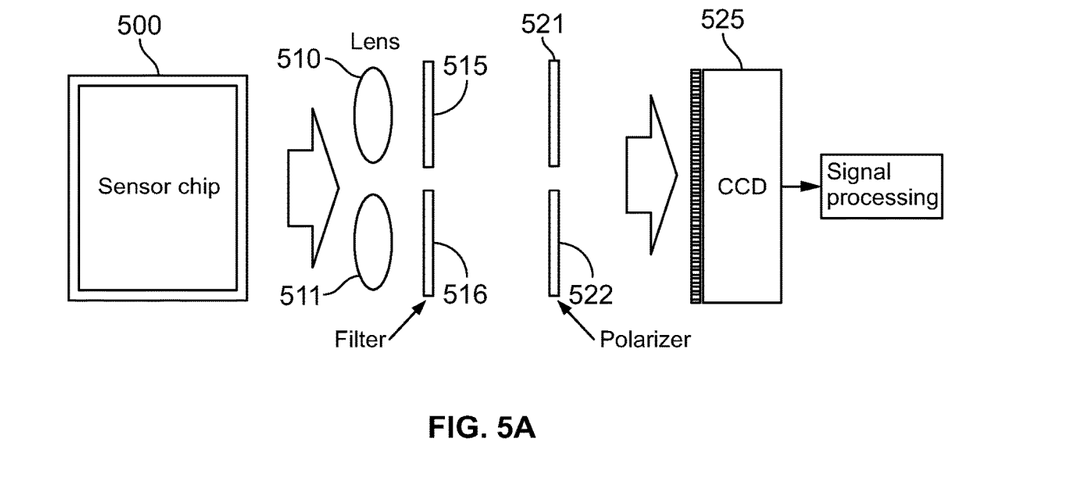
FIG. 5A is a schematic diagram showing an optical configuration for an embodiment of the present invention that separates different angular frequencies (lens), wavelengths (filter) and polarizations (polarizer) before projection.
Figure 5B:
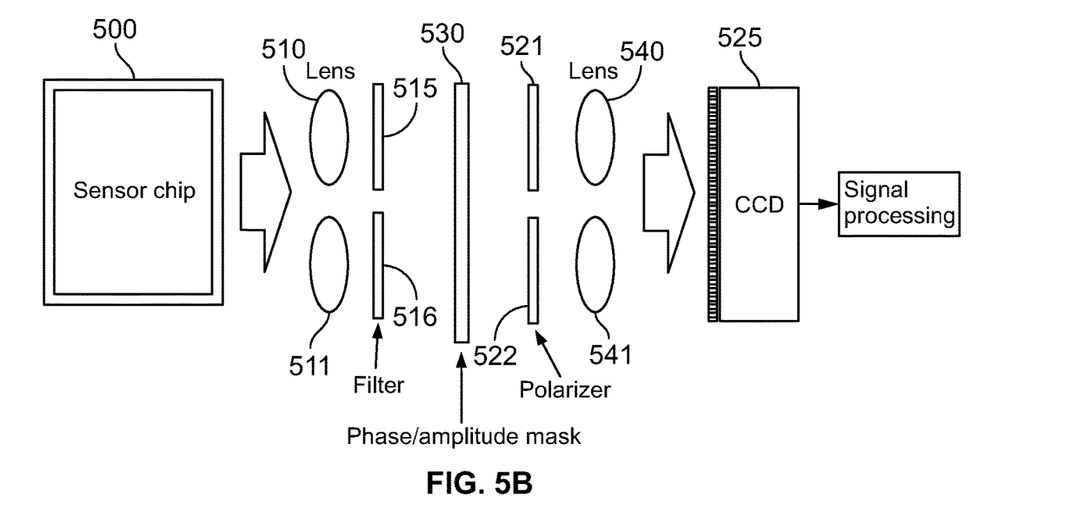
FIG. 5B is a schematic diagram showing an optical configuration for an embodiment of the present invention that modulates the phase and amplitude of the output (in addition to separating different angular frequencies, wavelengths and polarizations) and transforms the resulting power distribution using one or more lenses (that generate a transformed distribution of angular frequencies).

As shown in FIGS. 5A-5B, in other embodiments, the output of the slab waveguide 500 may be collected through one or more lenses 510-511, one or more wavelength filters 515-516, one or more polarizers 521-522 and one or more phase and/or amplitude masks 530 (collectively referred to a "optical signal processing stage") that separate different wavelengths, spatial frequencies and polarizations before projection on the CCD. By optimizing the properties of the "optical processing stage," the projected powers on different pixel groups on the CCD will be proportional to the concentration of the target molecules on the corresponding functional regions. FIG. 5A shows an optical configuration for an embodiment of the present invention that separates different angular frequencies (lens 510-511), wavelengths (filter 515-516) and polarizations (polarizers 521-522) before projection to CCD array 525. FIG. 5B shows an optical configuration for an embodiment of the present invention with more advanced optical signal processing stage compared to the structure set forth in the embodiment shown in FIG. 5A In this embodiment the phase and amplitude of the optical waves exiting the slab waveguide are modulated by use of phase/amplitude mask 530 and transformed in angular frequency domain by lens 540-541 before projection on the CCD.

Figure 6A:
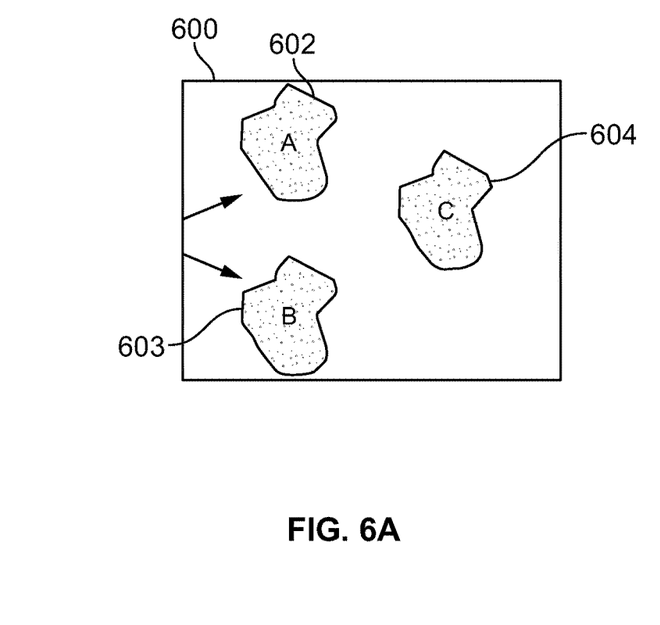
FIG. 6A shows a chip design for molecule detection that is a simple slab waveguide that is functionalized on the surface with predetermined patterns of trapping molecules (or functional polymers).

In yet other embodiments, one or more trapping regions may be distributed over the slab with a predetermined pattern/shape and spatial distribution that optimizes the impact of the surface index change on the device output through optical processing stage, CCD (photodetector array) and electronic processing stage. In one preferred embodiment, as shown in FIG. 6A, slab waveguide 600 may be functionalized on the surface with one or more predetermined patterns 602-604 of trapping sections or functional polymers. Trapping sections 602-604 are separated by non-functional region 605. As set forth above trapping sections or regions 602-604 which may be the same antibody of different antibodies, cells or functional polymers or any other substance configured to trap or entrain a subject target. Using one or more non-functional regions to separate a plurality of functional regions enhances the sensitivity of the device by creating more sensitive two-dimensional diffraction patterns as compared to functionalizing the entire surface of the waveguide.

In addition, the diffraction pattern of each trapping section or region may be compared and analyzed as discussed herein. This allows for the determination of which region is engaging and target which may be used to identify the target itself.

Figure 6B:
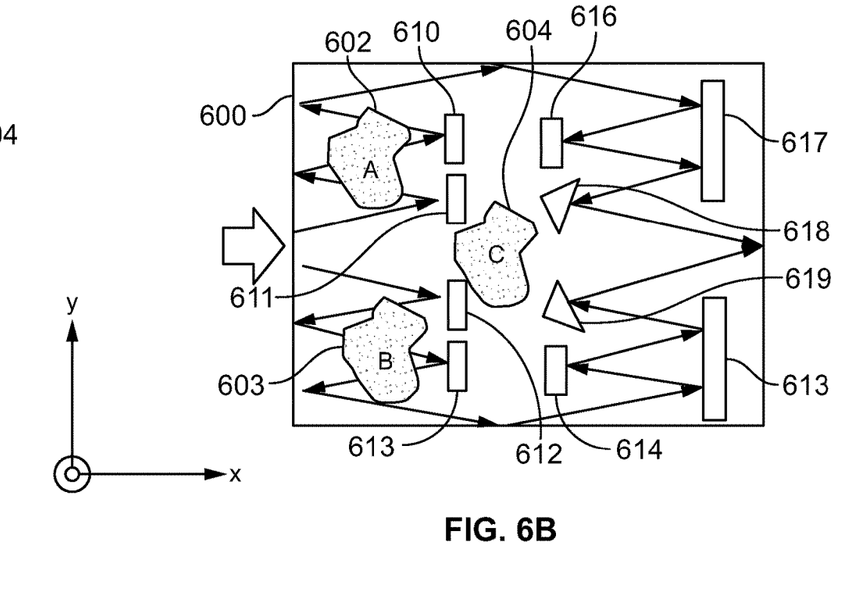
FIG. 6B shows a chip design for molecule detection that is a slab waveguide with arrangements that are specially designed for increasing the interaction path length within the slab.

In yet another embodiment, as shown in FIG. 6B, slab waveguide 600 may also include arrangements 610-619 that may be holes or openings or other structures that are designed for increasing the interaction path length. As shown, the arrangements may be rectangular, square or triangular in shape and configured to increase the interaction path length within the slab by repeatedly redirecting the optical beams within the slab.

In yet other embodiments, the present invention is configured so that a plurality of beams interfere with the output to form a diffraction pattern. Accordingly, the resulting optical power distribution will be sensitive to the biomarker concentration on each path. This allows for fabrication using conventional photolithographic techniques with micrometer resolution producing an active area that effectively supports a large number of multiple optical paths resulting in high sensitivity without sacrificing the response time.

In yet another embodiment of the present invention, the slab waveguide is configured to support two dimensional modes that can have a relatively large evanescent tail outside the waveguide. In the geometrical optical image, each mode can be considered as the collective propagation of several beams in a three dimensional space. Each beam that belongs to a certain mode follows a unique path. The effective refractive index along this path can be affected by the properties of the medium above the slab and right above that path. As such, if a different fraction of each path is functionalized with one or more different antibodies (or other analytes or trapping agents), upon attachment of the target, each beam will experience a different phase shift. Once all or some of the beams are combined in the output, the total output power will be extremely sensitive to the overall concentration of a target such as a biomarker in a solution that covers the slab.

In yet other aspects of the present invention, an important determining factor is the specific region of the slab that is covered with trapping sections. The location, shape, size and orientation of the pattern will determine the sensitivity of the optical output power. Moreover, as discussed above, separating the trapping regions by non-functional regions also increases the sensitivity of the sensor.

Alternatively, the slab waveguide can be excited by an optical source comprised of a plurality of sources and also the output can consist of multiple lenses. In a preferred embodiment, the only limitation on the linewidth of the optical source is an equivalent coherent length larger than the largest optical path in the system.

Figure 7A:
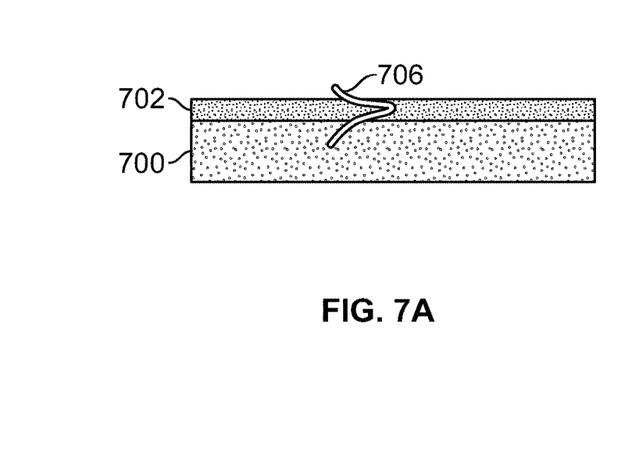
FIG. 7A is a schematic diagram illustrating a simple a thin high index layer on top of a low index substrate.
Figure 7B:
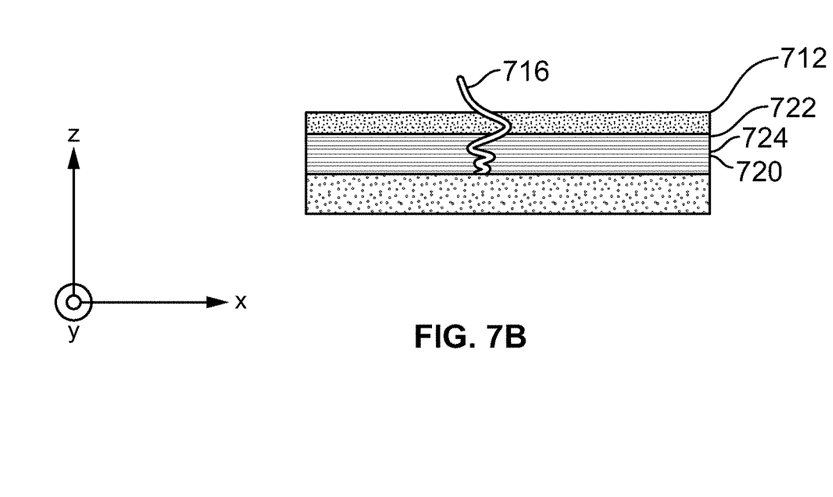
FIG. 7B is a schematic diagram illustrating a high index layer on top of a multilayer 1-D photonic crystal (specially designed alternating layers of high and low index materials along z-axis). The photonic crystal increases the penetration depth of the evanescent field on the top surface resulting in enhanced sensitivity.

FIGS. 7A and 7B show various ways in which a substrate and slab may be fabricated using different materials so long as they have enough optical transparency. In a preferred embodiment, slab 702 may have a larger refractive index as compared to substrate 700. In another preferred embodiment, substrate 700 may consist of a 1D photonic crystal layer that enhances light confinement in the waveguide layer 702 and enhances the evanescent field 706.

In yet another embodiment, as shown in FIG. 7B, the present invention provides a high index layer 712 on top of a multilayer 1-D photonic crystal 720 layer which may include alternating layers of high 722 and low 724 index materials along the z-axis. The photonic crystal increases the penetration depth of the evanescent field on the top surface with larger portion of the optical field being pushed along the z-axis to interact with target molecules or function polymers resulting in enhanced sensitivity.

Unlike High-Q microresonators, the level of optical loss that may be tolerated by the embodiments of the present invention is very large. So long as all the output intensity is above the sensitivity limit of the photodetector, the sensor works. In a High-Q resonant system, the optical loss should be low enough to support very long optical path lengths on order of 50 to 100 meters.

In addition to being used to measure or detect an antibody or analyte, the invention may also be used measure and or detect any type of cell, bacteria, virus, molecule or macromolecule. It can also monitor intra or extracellular activities (biochemical changes) for the cell culture grown on the slab waveguide.

In one embodiment, the input optical beam from one (or multiple) optical power sources are coupled to the propagating optical modes supported by a slab optical. This embodiment effectively splits the optical power split into a plurality of interfering optical beams propagating in the slab. In the output port of the slab, these modes form a diffraction pattern that can be projected and measured by a 2-D CCD array. The slab waveguide is designed to support a single optical mode along the z-axis (direction perpendicular to the slab). As the thickness of the slab is smaller than the wavelength of the optical source(s) a considerable portion of the optical field associated with slab modes leaks out to the surrounding environment as an evanescent field. As such, the optical phase of the propagating mode(s) is sensitive to the refractive index and absorption of the medium covering the slab. This results in a power distribution over the diffraction pattern exiting the output port that is sensitive to the refractive index and absorption of the medium near the slab top-surface.

The slab provided by the various embodiments of the present invention may be used for detecting the molecules within the volume covered by the evanescent optical field above the slab. The presence of the molecules induces detectable changes in the diffraction pattern that can be detected after processing in the optical and/or electronic domain. The slab waveguide can be illuminated with one or more optical sources through one or several waveguides. The output power that exits the slab is collected by one or more lenses and after passing through filters and polarizers, if needed, to form a diffraction pattern on a sensor such as a CCD. After further electronic processing, the signal generated by the CCD will be proportional to the concentration of target molecules on the slab. The optical filters and polarizers are used to select the wavelength range and polarizations that result in maximum sensitivity.

In another embodiment, the present invention provides a biosensor that may be used to detect biomolecules in an aqueous medium that covers the slab. In this embodiment, a specific area or multiple areas on the slab are functionalized with antibody molecules that can efficiently trap the target molecules in the liquid sample. The bound molecules interact with the optical modes through the evanescent field and change their effective refractive index where the surface is functionalized. As a result, the signature of binding events appear as changes in the diffraction pattern and consequently the output signal. By functionalizing multiple regions of the slab and further signal processing both in electronic and optical domain, multiple electronic signals proportional to different target molecules can be generated.

In another embodiment, the present invention provides a gas sensor that detects certain gas molecules with strong absorption near the source wavelength. In this embodiment, selective regions of the slab are covered by a blocking material that prevents the interaction with surrounding molecules. The absorption of the evanescent field by the gas molecules within the uncovered regions, results in measurable changes in the diffraction pattern. The uncovered regions of the slab can be also functionalized by several doped polymers with selective optical absorption sensitivity to target gas molecules. By processing the resulting diffraction pattern, first in the optical domain, and then electronic domain, multiple electronic signals proportional to different target molecules can be generated.

In another embodiment, the present invention provides an acoustic sensor that may be used to detect acoustic waves incident on the slab waveguide at a certain frequency range or ranges. In this embodiment, acoustic waves excite one or more mechanical modes of the slab and create a strain pattern over the slab. The resulting variation of the refractive index affects the diffraction pattern. By processing the resulting diffraction pattern first in the optical and then electronic domain, an electronic signal proportional to the strength of the acoustic wave will be generated.

While the foregoing written description enables one of ordinary skill to make and use what is considered presently to be the best mode thereof, those of ordinary skill will understand and appreciate the existence of variations, combinations, and equivalents of the specific embodiment, method, and examples herein. The disclosure should therefore not be limited by the above described embodiments, methods, and examples, but by all embodiments and methods within the scope and spirit of the disclosure.

What is claimed is:

1. A sensor comprising:
an optical slab waveguide having one or more target regions, said target regions configured to trap one or more targets of interest;
said optical slab waveguide adapted to receive one or more input optical beams from one or more light sources, wherein the one or more input optical beams generate a plurality of propagating optical waves in said optical slab waveguide;
said propagating optical waves interact with and are modified by said
one or more target regions to create an optical output wavefront at an output port of the slab waveguide; and
said optical output port is configured to allow the optical output wavefront to form a two-dimensional diffraction pattern upon exiting said output port, wherein a power distribution over said two-dimensional diffraction pattern is indicative of the interaction between said propagating optical waves and said one or more target regions.

2. The sensor of claim 1 further comprising a photodetector array wherein said two-dimensional diffraction pattern is formed on said photodetector array and wherein a resulting optical power distribution over a plurality of photodetectors in said photodetector array generates an electronic signal usable to determine a concentration of the one or more targets of interest trapped by said target regions.

3. The sensor of claim 2 wherein said photodetector array comprises a charge coupled device.

4. The sensor of claim 1 wherein said one or more target regions are functionalized with an antibody, polymer, cell, tissue, or biological material.

5. The sensor of claim 1 further including a plurality of spaced apart target regions separated by non-functionalized regions.

6. The sensor of claim 5 wherein at least two target regions have different configurations.

7. The sensor of claim 1 further including one or more optical manipulators that transform said optical output wavefront.

8. The sensor of claim 7 wherein said optical manipulators separate said optical wavefront into different angular frequencies.

9. The sensor of claim 7 wherein said one or more optical manipulators include filters, lens, polarizers, phase masks, amplitude masks or combinations thereof.

10. The sensor of claim 1 further comprising a substrate having a one dimensional photonic crystal layer on which said slab waveguide is disposed, wherein said photonic crystal layer is comprised of alternating layers of high and low refractive index material along a direction perpendicular to the top surface of the slab waveguide.

11. The sensor of claim 1 wherein said target regions include one or more functional polymers that directly interact with target gas molecules, said interaction of said gas and said polymers modifies the optical absorption or refractive index of the polymer.

12. A method of detecting targets of interest, the method comprising:
providing an optical slab waveguide having one or more target regions, said target regions configured to trap one or more targets of interest;
coupling one or more input optical beams generated by one or more light sources, to the optical slab waveguide to generate a plurality of propagating optical waves in said optical slab waveguide;
measuring an optical power distribution over a two-dimensional diffraction pattern formed by optical output wavefronts exiting the optical slab;
detecting the targets of interest based at least in part on the measured optical power distribution,
wherein the output wavefronts are generated by the propagating optical waves.

13. The method of claim 12 wherein the optical output wavefronts are generated by the plurality of propagating optical waves interacting with the one or more target regions.

14. The method of claim 12 wherein detecting the targets of interest comprises determining a changes in the measured optical power distribution the two-dimensional diffraction pattern.

15. The method of claim 12 wherein targets comprise molecules, cells, bacteria, viruses, or macromolecules in a medium covering the slab.

16. The method of claim 15 wherein the medium comprises a liquid or a gas.

17. The method of claim 12 wherein measuring optical power distribution over a two-dimensional diffraction pattern comprises projecting the two-dimensional diffraction pattern on a photodetector array and generating an electronic signal usable to determine a concentration of the one or more targets of interest trapped by said target regions.

18. The method of claim 12 wherein said one or more target regions are functionalized with an antibody, polymer, cell, tissue, or biological material.

19. The method of claim 12 further comprising transforming the optical output wavefronts using one or more optical manipulators.

20. The method of claim 12 further comprising a substrate having a one dimensional photonic crystal layer on which said slab waveguide is disposed, wherein said photonic crystal layer is configured to enhance an evanescent field formed above the slab waveguide.

* * * * *